US009880082B2

United States Patent
Esaki et al.

(10) Patent No.: US 9,880,082 B2
(45) Date of Patent: Jan. 30, 2018

(54) DETECTION DEVICE THAT CALCULATES A CENTER OF GRAVITY OF A CONTAINER GAP REGION

(71) Applicant: Hitachi High-Technologies Corporation, Minato-ku, Tokyo (JP)

(72) Inventors: Kanako Esaki, Tokyo (JP); Tatsuo Nakagawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 164 days.

(21) Appl. No.: 14/897,795

(22) PCT Filed: Jul. 2, 2014

(86) PCT No.: PCT/JP2014/067621
§ 371 (c)(1),
(2) Date: Dec. 11, 2015

(87) PCT Pub. No.: WO2015/002218
PCT Pub. Date: Jan. 8, 2015

(65) Prior Publication Data
US 2016/0109350 A1    Apr. 21, 2016

(30) Foreign Application Priority Data

Jul. 4, 2013 (JP) ................. 2013-140729

(51) Int. Cl.
*G01N 15/05* (2006.01)
*G01N 33/49* (2006.01)
(Continued)

(52) U.S. Cl.
CPC ........... *G01N 15/05* (2013.01); *G01N 15/042* (2013.01); *G01N 33/491* (2013.01);
(Continued)

(58) Field of Classification Search
CPC ... G01N 2015/0065; G01N 2035/0449; G01N 2035/00752; G01N 2035/0405;
(Continued)

(56) References Cited

U.S. PATENT DOCUMENTS 5,443,164 A  *  8/1995  Walsh ................... B07C 5/3416
                                                            198/836.1
6,673,316 B1     1/2004  Okamoto et al.
(Continued)

FOREIGN PATENT DOCUMENTS

JP      7-98239 A       4/1995
JP      9-133687 A      5/1997
(Continued)

OTHER PUBLICATIONS

International Search Report (PCT/ISA/210) issued in PCT Application No. PCT/JP2014/067621 dated Sep. 22, 2014 with English-language translation (four (4) pages).
(Continued)

*Primary Examiner* — Michael P Lapage
(74) *Attorney, Agent, or Firm* — Crowell & Moring LLP

(57) ABSTRACT

A detection device configured to detect each color of a plurality of components of a biological-sample is provided. The detection device executes the detection process with respect to the container which stores the sample containing the first and the second components. The detection device includes an image pickup device for picking up an image of the container, a background section serving as background of the image pickup section, and a detection section for detecting color of the first component of the sample. The container is disposed between the image pickup section and the background section. The detection section is configured to identify a first region of the first component having the label attached to the container as background, and a second
(Continued)

region of the first component having the background section as background so as to detect color information on the first component from at least one region of the first and the second regions.

11 Claims, 19 Drawing Sheets

(51) Int. Cl.
  *G01N 15/04* (2006.01)
  *G01N 15/00* (2006.01)
  *G01N 35/00* (2006.01)
  *G01N 35/04* (2006.01)
(52) U.S. Cl.
  CPC ............... *G01N 2015/0065* (2013.01); *G01N 2015/045* (2013.01); *G01N 2035/00752* (2013.01); *G01N 2035/0405* (2013.01); *G01N 2035/0406* (2013.01); *G01N 2035/0449* (2013.01)
(58) Field of Classification Search
  CPC ..... G01N 2035/0406; G01N 2015/045; G01N 35/00732; B01J 3/5453
  See application file for complete search history.

(56) References Cited

U.S. PATENT DOCUMENTS

| | | | |
|---|---|---|---|
| 8,194,235 | B2 | 6/2012 | Kosaka et al. |
| 2002/0134923 | A1* | 9/2002 | Watari ................ G01B 11/028 250/221 |
| 2005/0163354 | A1 | 7/2005 | Ziegler |
| 2006/0014295 | A1 | 1/2006 | Ziegler |
| 2006/0159224 | A1 | 7/2006 | Itoh |
| 2012/0140230 | A1* | 6/2012 | Miller .................. G01N 15/042 356/441 |
| 2013/0076882 | A1* | 3/2013 | Itoh ........................ G01N 21/25 348/77 |
| 2013/0306732 | A1* | 11/2013 | Berssen ........... G01N 35/00732 235/462.08 |
| 2015/0241457 | A1* | 8/2015 | Miller .............. G01N 35/00732 348/143 |

FOREIGN PATENT DOCUMENTS

| | | | | |
|---|---|---|---|---|
| JP | 9133687 | A * | 5/1997 | ............. G01F 23/28 |
| JP | 11-51746 | A | 2/1999 | |
| JP | 2000-088844 | A | 3/2000 | |
| JP | 2001-245874 | A | 9/2001 | |
| JP | 2004-37322 | A | 2/2004 | |
| JP | 2005-017219 | A | 1/2005 | |
| JP | 2005-140615 | A | 6/2005 | |
| JP | 2005-345373 | A | 12/2005 | |
| JP | 2006-200949 | A | 8/2006 | |
| JP | 2010-38659 | A | 2/2010 | |
| JP | 2011-247635 | A | 12/2011 | |
| JP | 2012-159318 | A | 8/2012 | |
| JP | 2013-242246 | A | 12/2013 | |
| WO | WO/2012/069345 | * | 5/2012 | ............. G01N 35/00 |

OTHER PUBLICATIONS

English-language translation of Japanese Office Action issued in counterpart Japanese Application No. 2013-140729 dated Jan. 16, 2017 (three (3) pages).

* cited by examiner

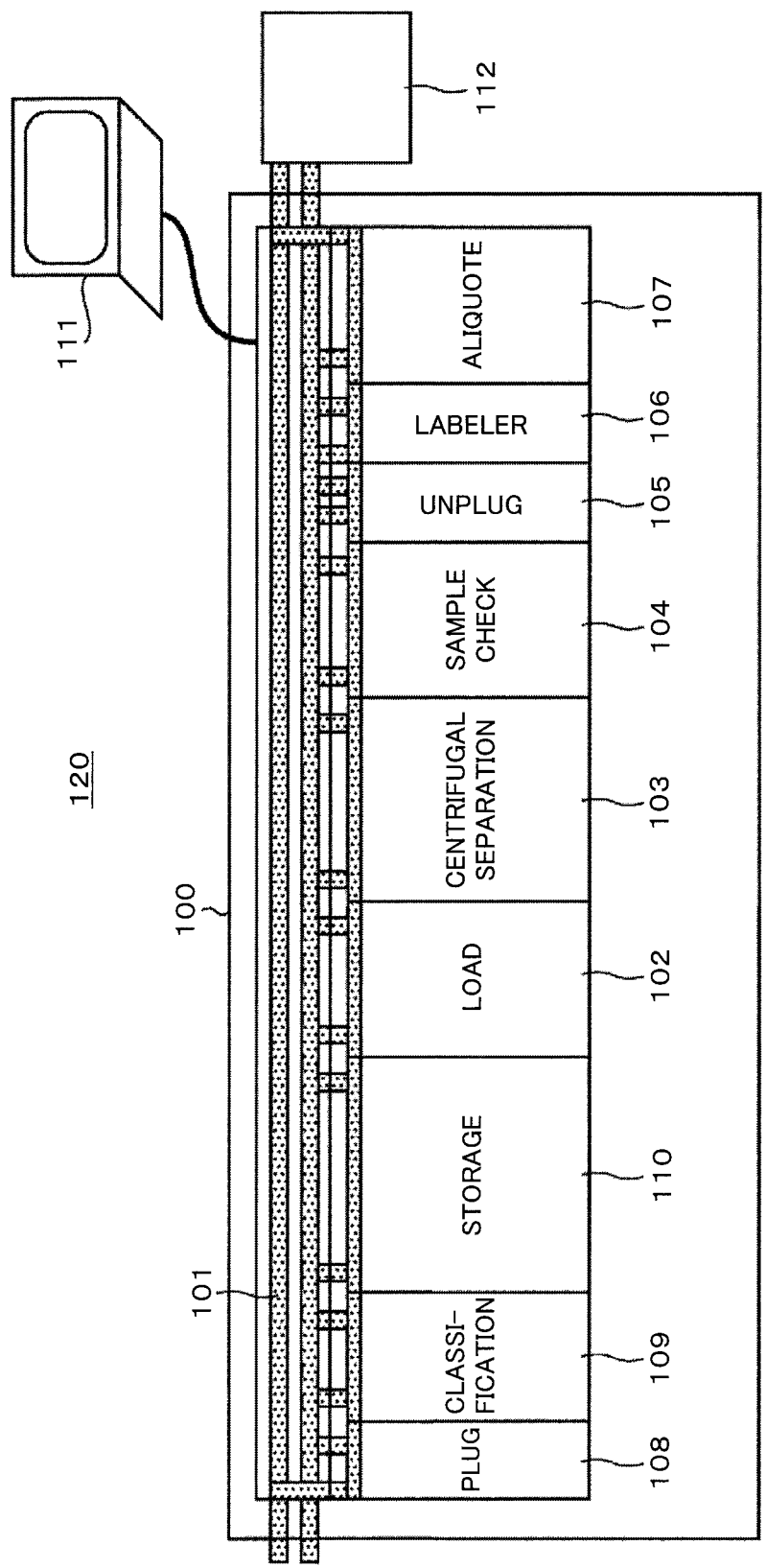

FIG. 2A
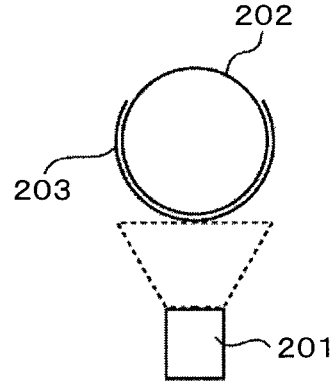
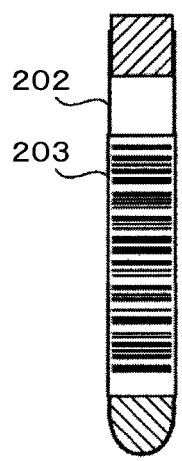
FIG. 2B
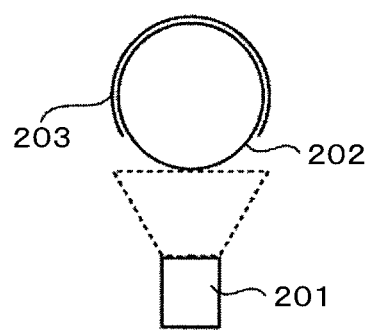
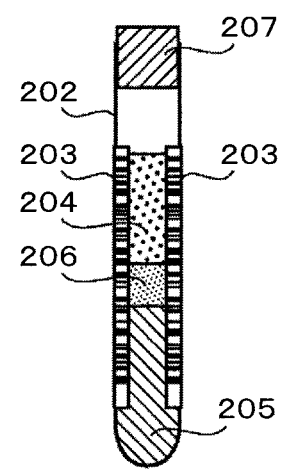

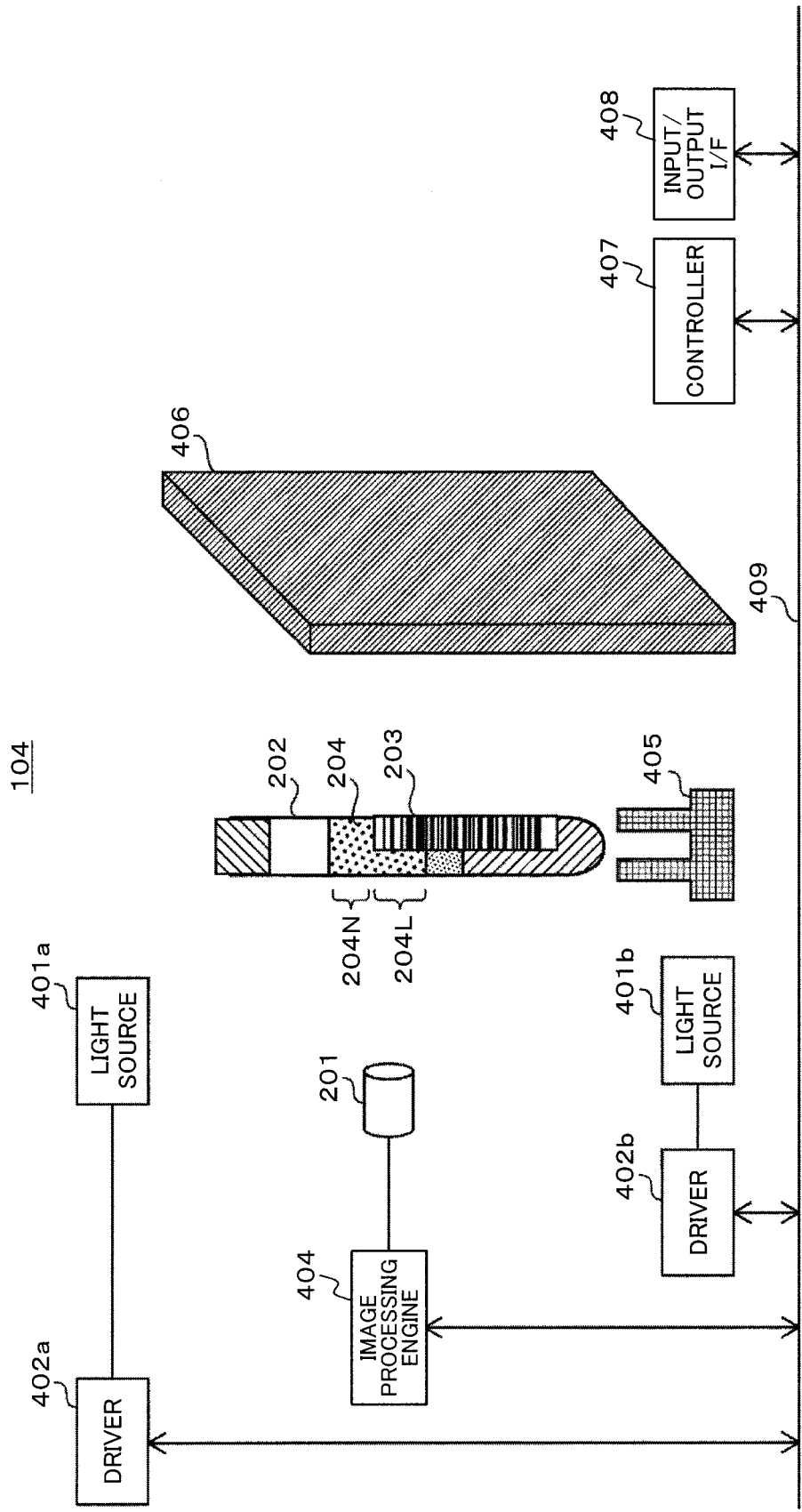

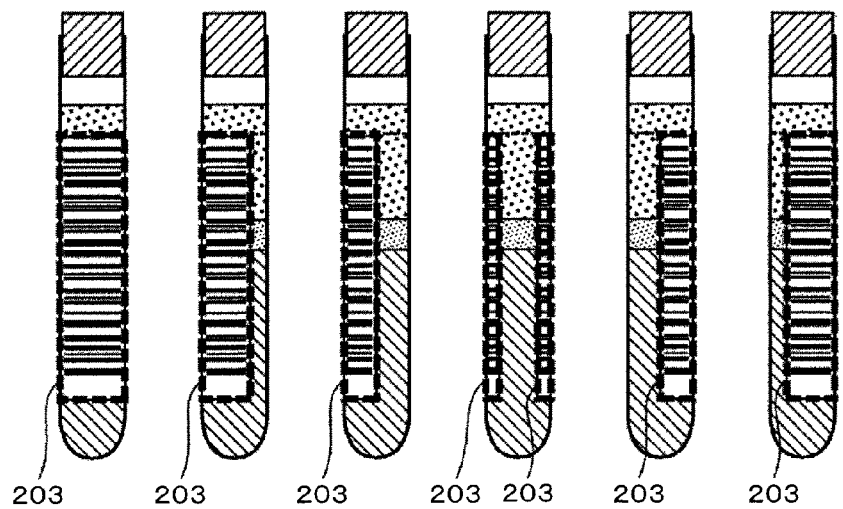
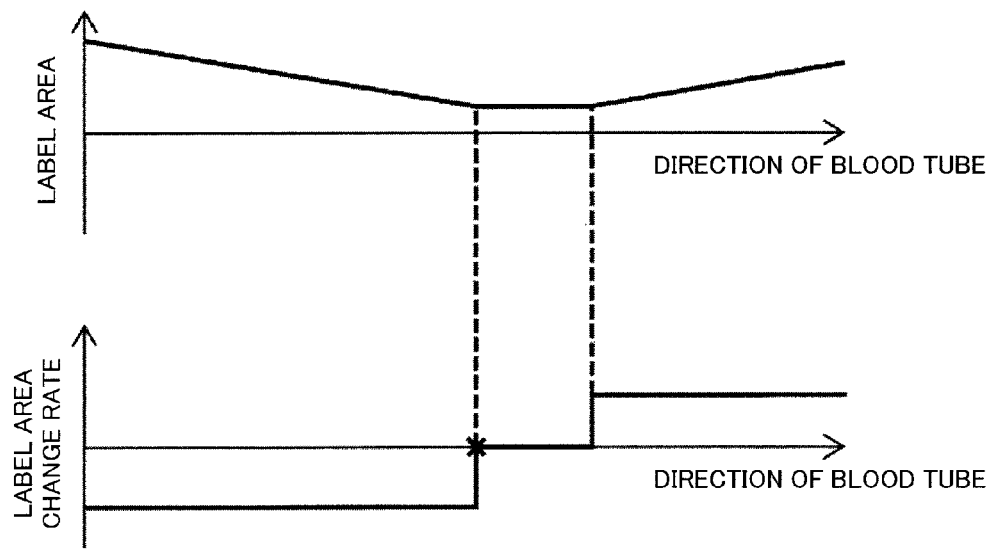
FIG. 10G

DETECTION DEVICE THAT CALCULATES A CENTER OF GRAVITY OF A CONTAINER GAP REGION

TECHNICAL FIELD

The disclosure relates to a detection device applicable to a detector for detecting each color and amount of a plurality of components that constitute a sample and a biological-sample analysis device.

BACKGROUND ART

Generally, the technique for analyzing components that constitute a biological sample has been introduced. The biological sample of a patient is processed in a container exclusively used for the aforementioned technique. Upon use of a blood sample, the collected blood is fed into a blood tube which has been preliminarily filled with a separating agent. Thereafter, the blood tube is subjected to centrifugal separation so that the blood is separated into clot and serum layers. Then the serum as the component necessary to the analysis is extracted.

Recently, the inspection item measurable by means of the serum has been diversified. As a result, a large number of automatic analyzers have been provided, leading to significantly increased samples. The aforementioned situation has necessitated pre analysis to be executed before loading the biological sample into the automatic analyzer, or the system for automatically transporting the sample to the automatic analyzer.

The process for detecting index and liquid amount of the serum has been known as the pre analysis. If the serum as the sample is colored different from the normal color (pale yellow), for example, the hemolysis (red), jaundice (dark yellow) and chyle (milky-white), such sample may cause an error in the automatic analyzer operated in accordance with the absorbance as the measurement principle. In order to avoid the error, it is necessary to remove the sample indexed as hemolysis, jaundice and chyle. In the case of hemolysis, it is necessary to require the physician to carry out the blood collection again. If the liquid amount of the serum is insufficient for the analysis, the aliquot amount has to be determined by prioritizing the analytical items. Furthermore, the probe may thrust through the separating agent during aliquot, resulting in such error as clogging. It is therefore necessary to recognize insufficiency in the liquid amount of the serum before aliquot process. In one of methods practically utilized in the laboratory, the label is applied to a surface of the blood tube, on which important information such as patient ID, personal information, parameters necessary for device operation is provided. Patent Literature 1 discloses the art for handling the labeled blood tube, which is configured to identify the unlabeled surface by checking the light receiving level of the photodetector of the optical sensor during horizontal rotation of the blood tube by the rotation mechanism, and to have image data of the identified surface picked up by a camera for calculating the blood volume.

CITATION LIST

Patent Literature

Patent Literature 1: Japanese Unexamined Patent Application Publication No. 2010-038659

SUMMARY OF INVENTION

Technical Problem

Patent literature 1 discloses calculation of blood volume in reference to image data of the unlabeled surface picked up by the camera in consideration of the blood region including the labeled region and unlabeled region in the radial direction of the blood tube coexisting with each other. The blood region along the blood tube axis direction also includes the labelled region and the unlabeled region coexisting with each other. Especially, the centrifugally separated serum exhibits high transmittance. The scattered light from an object to the rear of the blood tube seen from the camera is incident on the camera. When picking up an image of the unlabeled surface by the camera in the aforementioned circumstances, there may be mixture of the serum region having the label located as background, and the serum region having a background plate located to the rear of the blood tube as background when seen from the camera. Colors of both regions in the images picked up by the camera become different in spite of the same serum index. Accordingly, mixture of labeled and unlabeled regions in the axial direction of the blood tube has to be considered for the purpose of accurately acquiring the color information and amount of the serum.

It is an object of the present invention to provide a detection device for accurately detecting the color information of a sample either in the labeled or unlabeled state.

The aforementioned and other objects and novel characteristics of the disclosure will be clarified by the following description and accompanying drawings.

Advantageous Effects of Invention

The representative disclosure will be briefly summarized as below.

The detection device stored in the container is configured to subject the sample containing a first component and a second component to the detection process. The detection device includes an image pickup section for picking up an image of the container, a background section located as background of the image pickup section, and a detection section for detecting color of at least one of the components of the sample. The container is disposed between the image pickup section and the background section. The detection section identifies a first region of the first component having a label attached to the container as background, and a second region of the first component having the background section as background so that color information on the first component is detected from at least one of the first and second regions.

The detection device is configured to allow highly accurate detection of the color information on the sample consisting of a plurality of components.

BRIEF DESCRIPTION OF DRAWINGS

FIG. 1 is a view representing an overall structure of a biological-sample analysis device according to a first embodiment.

FIGS. 2A and 2B are explanatory views representing a relationship between a camera and a direction of a label attached to a blood tube.

FIG. 4 is a view representing a structure of a sample check module according to the first embodiment.

FIGS. 10A-10G are explanatory views representing change in the label area in accordance with varying direction of the blood tube according to the second embodiment.

DESCRIPTION OF EMBODIMENTS

Figure 3A:
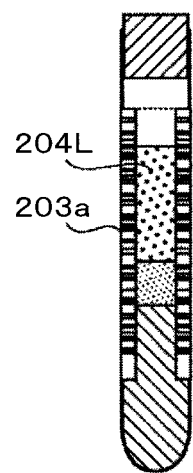
FIGS. 3A-3C are explanatory views representing a positional relationship between a serum region and the label attached to the blood tube surface.

Embodiments and examples will be described referring to the drawings. In overall drawings for explaining the embodiments and examples, each component with the same function will be designated with the same sign, and repetitive explanation thereof, thus will be omitted.

Figure 21:
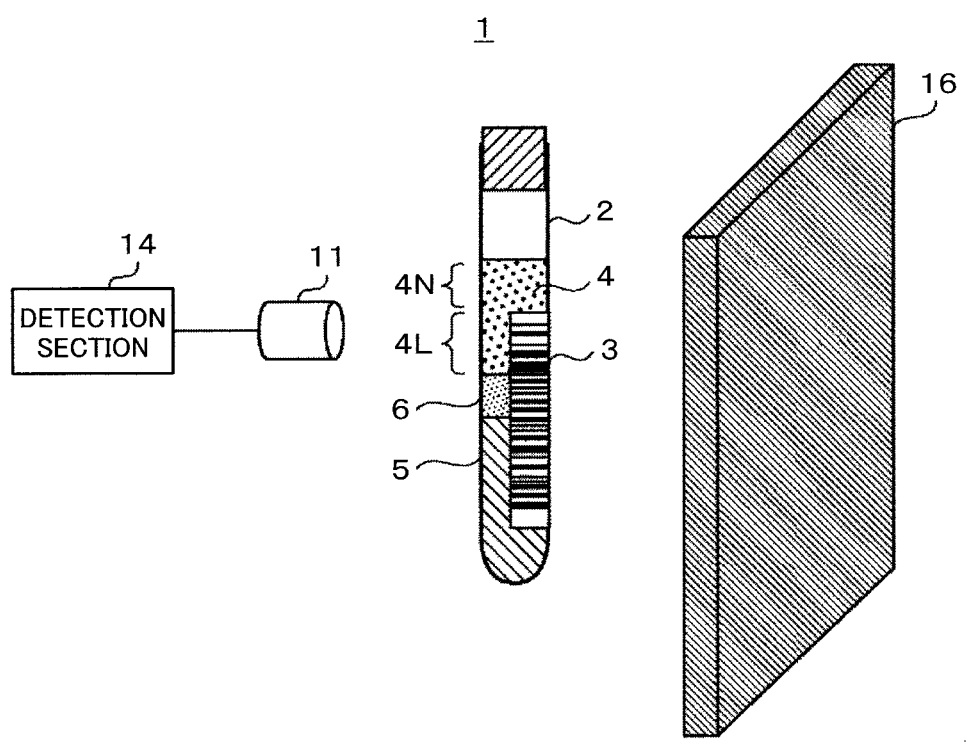
FIG. 21 is a view representing a structure of a detection device according to an embodiment.

FIG. 21 illustrates a structure of a detection device according to the embodiment. A detection device 1 is configured to execute the detection process with respect to a container 2 for storing a sample containing a first component 4 and second components 5, 6. The second component does not have to be double layered. The detection device 1 includes an image pickup section 11 for picking up an image of the container 2, a background section 16 serving as a background of the image pickup section 11, and a detection section 14 for detecting color of the first component 4 of the sample. The container 2 is disposed between the image pickup section 11 and the background section 16. The detection section 14 identifies a first region 4L of the first component 4 having the label 3 attached to the container 2 as background, and a second region 4N of the first component 4 having the background section 16 as background, and detects the color information on the first component 4 from at least one of the first region 4L and the second region 4N.

The above-configured detection device allows highly accurate detection of each color and amount of a plurality of components that constitute the sample.

First Embodiment

A biological-sample analysis device according to a first embodiment will be described referring to FIGS. 1 to 6. FIG. 1 illustrates an overall structure of the biological-sample analysis device according to the first embodiment. The device is configured to execute pre analysis of the biological sample (blood) collected from a patient so as to be analyzed by an automatic analyzer. A biological-sample analysis device 120 includes a pre analytical system 100, a control PC 111 for overall control of the pre analytical system 100, and an automatic analyzer 112 connected to the pre analytical system 100 for analyzing the component of the biological sample. The pre analytical system 100 includes a plurality of basic modules such as a transport line 101, a load module 102, a centrifugal separation module 103, a sample check module (detection device) 104, an unplug module 105, a labeler 106 such as a bar code, an aliquoter module 107, a plug module 108, a classification module 109, and a storage module 110.

The load module 102 accommodates the sample (blood tube filled with blood), and the centrifugal separation module 103 subjects the loaded sample to centrifugal separation. The sample check module 104 detects index and liquid amount of the serum. The unplug module 105 uncaps the centrifugally separated sample. The aliquoter module 107 executes the aliquot process of the centrifugally separated sample for analysis by the automatic analyzer 112. The labeler 106 serves to apply bar codes to an aliquot container. The plug module 108 caps the sample. The storage module 110 stores the plugged sample. The classification module 109 classifies the aliquot sample container.

The sample analysis flow will be described below. The blood tube is used for collecting blood (whole blood) of the patient. The blood tube is loaded in the load module 102 of the pre analytical system 100. Process steps of the blood collection and loading are manually executed by the user. The subsequent steps will be automatically executed by the pre analytical system 100. Generally, a nursing staff will be in charge of the blood collection, and the laboratory technician will be in charge of the loading. There may be the case where the blood collection is carried out in a facility other than the one where the biological-sample analysis device is installed.

The transport line 101 involves the transport operation. The loaded blood tube is transported to the centrifugal separation module 103 for centrifugal separation. The separation agent has been preliminarily added to the blood tube so that the sample is separated into a clot layer with relatively high specific gravity, and a serum layer with relatively low specific gravity usable for the blood analysis. The centrifugally separated sample is transported to the sample check module 104 for detecting index and liquid amount of the serum. The detection method will be described later in detail. If it is determined that the serum is indexed as hemolysis, jaundice, and chyle, the sample is transported to the classification module 109 for classifying the sample as an error sample. Meanwhile, if it is determined that the serum is indexed as normal, and its liquid amount is detected, the sample is transported to the unplug module 105 for uncapping the centrifugally separated sample. The sample is then transported to the aliquoter module 107. Simultaneously, the aliquot container to which the bar code is applied by the labeler 106 is transported to the aliquoter module 107. Then aliquot of the sample into the aliquot container is carried out in accordance with the information on the liquid amount of the serum detected by the sample check module 104. Upon completion of aliquot, the sample is transported to the plug module 108 for capping the sample, which then will be stored in the storage module 110. The stored aliquot containers are transported to the automatic analyzer 112 for analysis of the respective components.

The label marked with personal information and the like is attached to the surface of the blood tube of the sample to be transported to the sample check module 104. Upon detection of color and liquid amount of the serum by receiving visible light through the camera, the label position has to be taken into account. FIG. 2 illustrates the relationship between the camera and direction of the label attached to the blood tube. The upper section of FIG. 2 is a top view, and the lower section is a side view. FIG. 2(A) represents that a label 203 attached to the blood tube (container) 202 is directed toward the camera 201. FIG. 2(B) represents that the label 203 attached to the blood tube 202 is directed at the far side from the camera 201. FIG. 2(A) indicates that the image of the serum region cannot be picked up by the camera 201 because of interruption by the label. FIG. 2(B) indicates that the image has to be picked up through the gap between the labels 203. The blood (sample) in the blood tube 202 is separated into an upper section as the serum (serum region, first component) 204 and a lower section as the clot (clot region, second component) 205 by the separating agent 206. The blood tube 202 is plugged with a cap 207.

Figure 3B:
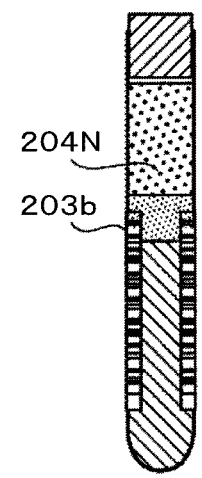
Figure 3C:
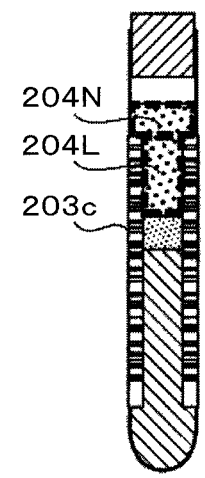

FIG. 3 represents the positional relationship between the serum region and the label attached to the blood tube surface. FIG. 3(A) shows the state where a label 203*a* is attached to cover substantially the whole area of the serum region in the longitudinal direction. FIG. 3(B) shows the state where a label 203*b* is attached so as not to cover the whole area of the serum region in the longitudinal direction. FIG. 3(C) shows the state where a label 203*c* is attached so that the serum region is partially covered in the longitudinal direction. Because of high transmittance of the serum, the camera may receive incidence of scattered light from the object to the rear of the blood tube. In the case of FIG. 3(A), only a serum region 204L having the label 203*a* as background is picked up by the camera. In the case of FIG. 3(B), only a serum region 204N having a background plate (background section) located to the rear of the blood tube as background is picked up by the camera. In the case of FIG. 3(C), the serum region 204L having the label 203*c* as background, and the serum region 204N having the background plate as background coexist. In spite of the same serum, the color of the serum image picked up by the camera in the serum region having the label as background is different from the one in the serum region having the background plate as background.

In the case where color of the background plate is the same as that of the label, the color of the serum region having the label as background becomes the same as the one having the background plate as background so long as the serum index is the same. Besides the black background plate, the illumination light will reflect on the background plate, which forms shadows of the cap and label of the blood tube in the serum region. As a result, the color difference between the normal serum and the serum indexed as hemolysis, jaundice, and chyle is insufficient. Even in the use of the black background plate, which is different in color from the label to allow prevention of the illumination light reflection, it is still required to detect the index and the liquid amount of the serum. In the second to the sixth embodiments subsequent to the first embodiment, the following configuration allows the use of the black background plate for the image pickup so that the index and the liquid amount of the serum are detected regardless of labeled/unlabeled state.

It is preferable to use the background plate which prevents reflection of the illumination light. Specifically, for example, the background plate with reflectance of 10% or lower in the visible light region may be used. The color of the background plate is not limited to black. It is possible to use the background plate in the color complementary to that of the label so as to clearly distinguish the labeled region from the unlabeled region.

FIG. 4 shows a structure of the sample check module according to the first embodiment. A sample check module (detection device) 104 includes light sources 401*a*, 401*b*, light source drivers (drivers) 402*a*, 402*b*, a camera (image pickup section) 201, an image processing engine (detection section) 404, a blood tube holder (holding section) 405, a background plate (background section) 406, a controller 407, an input/output interface (I/O I/F) 408, and a data bus 409.

The light sources (irradiation elements) 401*a*, 401*b* each serving as the irradiation section irradiate light rays from upper and lower front sides of the blood tube 202, respectively. The LED light source which emits light with high intensity and high directivity may be used for the light sources 401*a*, 401*b*. The visible light with wavelength ranging from substantially 400 nm to 700 nm may be employed. The light source drivers 402*a*, 402*b* as power sources are used for driving the light sources 401*a*, 401*b*.

Light rays irradiated from upper and lower sides, that is, upper and lower front sides of the blood tube 202 ensure to make the intensity distribution of incident light on the blood tube uniform compared with the use of the single light source. Making the light intensity distribution uniform allows acquisition of the serum color information more accurately. As another embodiment of the light source arrangement, it is possible to irradiate light rays from left and right sides, that is, left and right front sides of the blood tube 202. The lateral light irradiation from the left and right front sides will never form the shadow of the cap of the blood tube in the serum region. This makes it possible to accurately provide the serum color information.

The camera 201 picks up a two-dimensional overall image of the blood tube 202. It is assumed that the camera 201 is positionally related to direction of the label 203 attached to the blood tube 202 so that the image of the sample in the blood tube 202 is picked up through the gap between the labels 203 as shown in FIG. 2(B). In this case, the light rays irradiated from the light sources 401*a*, 401*b* transmit through the blood tube 202 while having the wavelength partially absorbed by the serum 204 in the blood tube 202, and partially transmitting through the serum 204. The transmitted light further transmits through the blood tube 202, and scatters on the label 203 attached to the surface of the blood tube 202. The scattered light transmits through the blood tube 202, the serum 204, and the blood tube 202 again so as to be incident on the camera 201. The image processing engine 404 is configured to process the image picked up by the camera 201 for extracting the serum region, for example, so as to identify the position and color of the serum region.

The input/output interface 408 is employed as the interface upon display of the detected serum index/amount, transmission of data, and input of parameters for the serum index/amount from the control PC 111. The controller 407 is configured to execute entire control of the sample check module 104.

Figure 5:
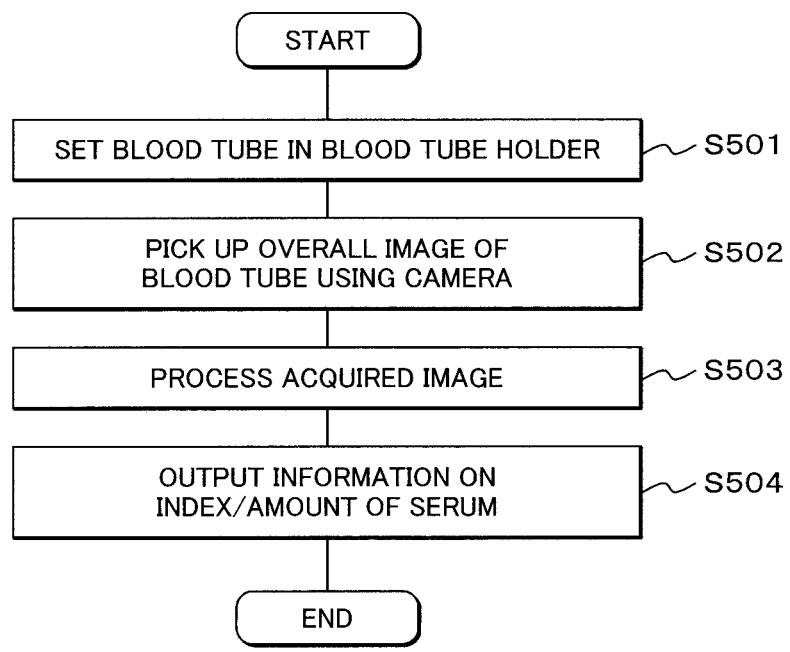
FIG. 5 is an operation flow of the sample check module according to the first embodiment.

FIG. 5 shows an operation flow of the sample check module according to the first embodiment. The labeled blood tube 202 is set in the blood tube holder 405 (step S501). Then the overall image of the blood tube 202 is picked up by the camera 201 (step S502). The picked up image varies with the positional relationship between the serum region and the label in the blood tube axis direction as shown in FIGS. 3(A) to 3(C). The image picked up by the camera 201 is processed by the image processing engine 404 (step S503). Information with respect to index and amount of the serum detected through the image processing is output (step S504).

Figure 6:
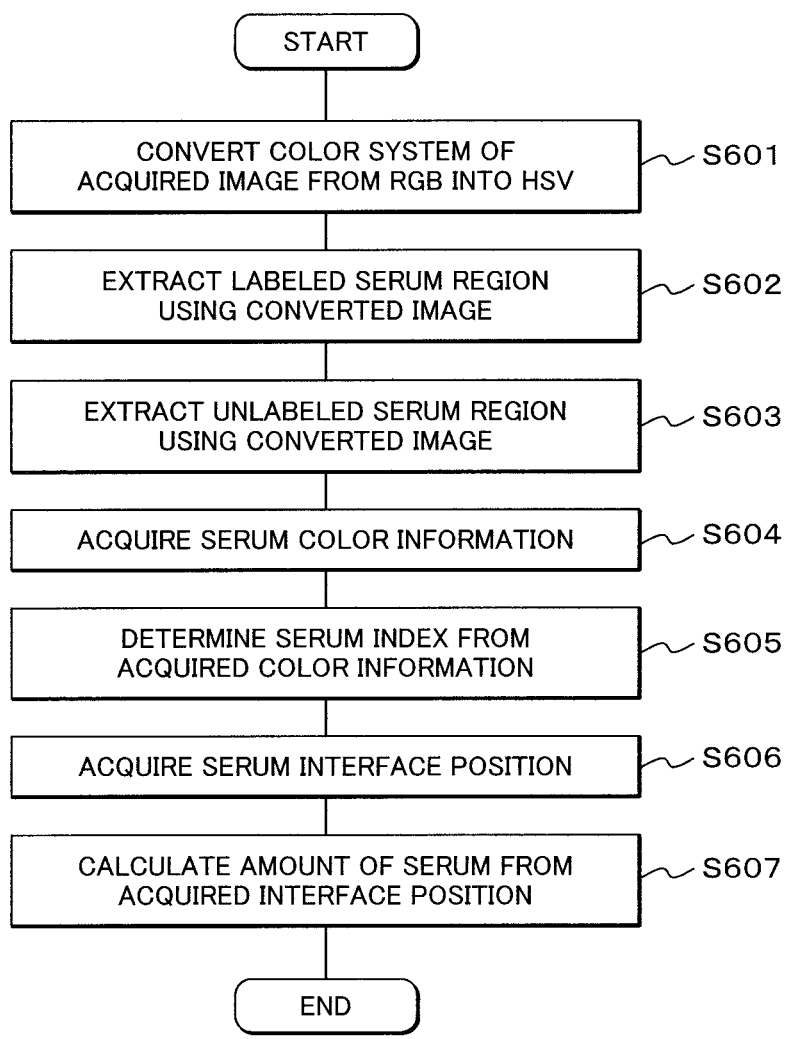
FIG. 6 is an operation flow for detecting index and amount of the serum according to the first embodiment.

FIG. 6 shows an example of the image processing flow. The color system of the acquired image is converted from RGB to HSV (step S601). The HSV color system has been known as being similar to the color perception process of human. It is therefore suitable for automating identification of the serum index, which has been manually executed conventionally. The image having the color system converted into HSV is used to extract the labeled serum region 204L as the one having the label as background (step S602). The unlabeled serum region 204N having the background plate 406 to the rear of the blood tube 202 as background is also extracted (step S603). If the picked up image shows only the serum region 302a having the label as background as shown in FIG. 3(A), the unlabeled serum region 204N is not extracted. If the picked up image shows only the serum region 301b having the background plate 406 to the rear of the blood tube 202 as background as shown in FIG. 3(B), the labeled serum region 204L is not extracted. If the image contains the serum region 302c having the label as background and the serum region 301c having the background plate as background, both the labeled serum region 204L and the unlabeled serum region 204N will be extracted.

The labeled serum region (first region) 204L and the unlabeled serum region (second region) 204N may be extracted by the process using a specific threshold value of the HSV color system. Specifically, the threshold values of the HSV color system are preliminarily set for extracting the labeled serum region 204L having the label as background, and extracting the unlabeled serum region 204N having the background plate 406 to the rear of the blood tube 202 as background, respectively. The process using the threshold values is executed so as to extract the labeled serum region 204L and the unlabeled serum region 204N, respectively. It is assumed to preliminarily set the threshold values used for extracting the labeled serum region 204L and the unlabeled serum region 204N, respectively. The threshold values may be changed in accordance with type of the blood tube 202, luminous energy of the light sources 401a, 401b, setting values of the camera 201 and the like. The different material may be used for forming the wall surface of the blood tube 202 depending on its type, resulting in different light transmittance. Therefore, the resultant image picked up by the camera 201 may exhibit a different color in spite of the same serum. The threshold value for extraction of the region is adjusted in accordance with the type of the blood tube 202 so as to allow accurate extraction of the serum region 204.

The serum color information is acquired after extracting the labeled serum region 204L and the unlabeled serum region 204N (step S604). Since the labeled serum region 204L is colored differently from the unlabeled serum region 204N, the color information is acquired from any one of those regions. For example, the mean color value in the labeled serum region 204L is acquired as the serum color. Generally, there are a large number of blood tubes each having the label attached to the back surface of the serum region. It is therefore effective to acquire the color information from the labeled serum region 204L.

Acquisition of the color information is not limited to the method as described above. It is possible to acquire the color information from the unlabeled region 204N. It is also possible to select the region from the above-described serum regions, from which the color information is acquired depending on the positional relationship between the serum region 204 and the label 203. For example, it is possible to acquire the color information from the labeled region 204L in the case of the positional relationship as shown in FIG. 3(A). It is also possible to acquire the color information from the unlabeled serum region 204N in the case of the positional relationship as shown in FIG. 3(B). The color information may be acquired from any one of the regions in the case of the positional relationship as shown in FIG. 3(C). The color information may be acquired from the serum region of a wider area.

The color information is acquired by calculating the mean value. However, it is possible to acquire the color information by calculating the median, variance and the like in an unlimited manner. In any case, the color information is acquired using the information with respect to the labeled serum region 204L and the unlabeled serum region 204N.

The serum index is determined from the acquired information (step S605). The determination with respect to the serum index is made using the threshold value for normality, hemolysis, jaundice, and chyle. The threshold value is preliminarily set by aligning the label 203 as background with the serum region. The preliminarily set threshold values are compared with the acquired serum color information so as to determine the serum index.

It is also effective to set the threshold value for determining the serum index by aligning the background plate 406 to the rear of the blood tube 202 as background with the serum region. It is possible to determine the serum index in the case only of the unlabeled serum region 204N as shown in FIG. 3(B).

The threshold value for determining the serum index may be changed in accordance with type of the blood tube 202, luminous energy of the light sources 401a, 401b, and setting values of the camera 201. The different material may be used for forming the wall surface of the blood tube 202 depending on its type, resulting in different light transmittance. Therefore the resultant image picked up by the camera 201 exhibits a different color in spite of the same serum. The threshold value for extraction of the region is adjusted in accordance with the type of the blood tube so as to allow determination of the serum index more accurately.

The serum interface position is acquired for calculating the serum amount (step S606). The uppermost part and the lowermost part of the serum region have to be extracted in order to acquire the serum interface position. The acquisition is executed by using the labeled serum region 204L and the unlabeled serum region 204N, both of which have been extracted. Specifically, for example, the combined region of the labeled and the unlabeled regions (binding region) is calculated so as to acquire the serum interface from the coordinate information on the interface between the binding region and the region thereabove (vacuum), and the interface between the binding region and the region therebelow (separating agent 206). Based on the acquired interface position, the serum amount is calculated using parameters such as diameter of the blood tube 202 (step S607).

The information on the calculated serum index and the serum amount will be controlled by the controller 407, and output to the control PC 111 via the input/output interface 408 (step S504). Such information is used for elimination of the error sample and determination with respect to insufficiency of serum amount.

As described above, the labeled and unlabeled serum regions are respectively extracted to acquire the color information from the labeled serum region. This makes it possible to make accurate determination of the serum index. The serum interface is calculated from the labeled and the unlabeled serum regions to accurately acquire the serum amount. The method according to the embodiment ensures accurate acquisition of the index and amount of serum irrespective of the label position in the blood tube axis direction.

Second Embodiment

In the first embodiment, the relationship between the camera and direction of the label attached to the blood tube is established so that an image of the sample in the blood tube is picked up through the gap between the labels as shown in FIG. 2(B). However, the sample held in the blood tube holder, which has been transported to the sample check module is not always kept in the state as shown in FIG. 2(B). This embodiment will describe the method of providing the image in the state as shown in FIG. 2(B) regardless of the relationship between the camera and direction of the label attached to the blood tube. The biological-sample analysis device to be described in the second embodiment is basically the same as the biological-sample analysis device 120 as described in the first embodiment except the sample check module.

Figure 7:
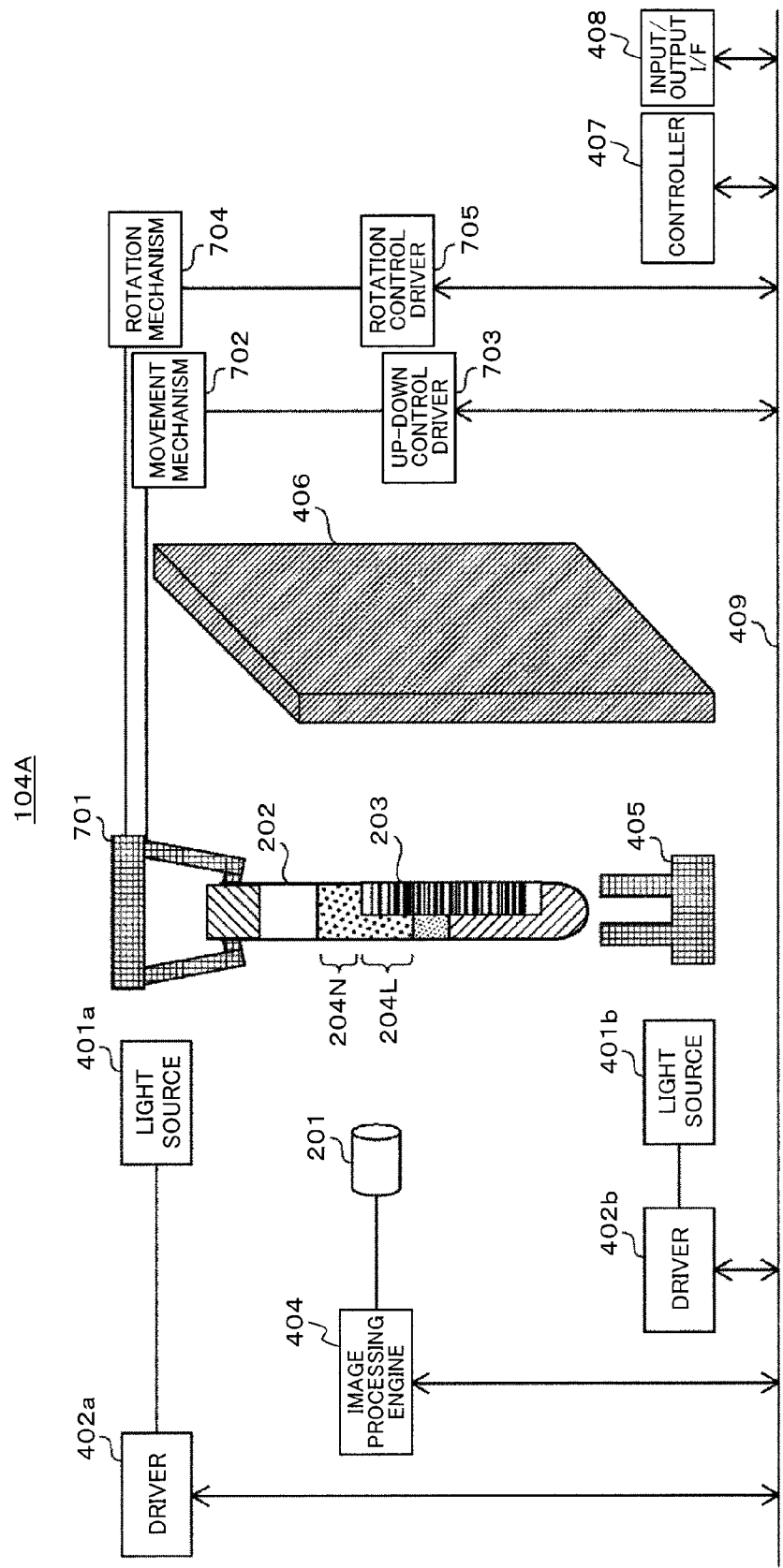
FIG. 7 is a view representing a structure of the sample check module according to a second embodiment.

FIG. 7 shows a structure of the sample check module according to the second embodiment. The sample check module (detection device) 104A includes the light sources 401a, 401b, the light source drivers 402a, 402b, the camera (image pickup section) 201, the image processing engine (detection section) 404, the blood tube holder (holding section) 405, the background plate (background section) 406, the controller 407, the input/output interface 408, the data bus 409, a grip mechanism 701, a movement mechanism 702, an up-down control driver 703, a rotation mechanism 704, and a rotation control driver 705.

The light sources (irradiation elements) 401a, 401b constituting the irradiation section irradiate light rays from the upper front and lower front sides of the blood tube 202 so that the camera 201 picks up a two-dimensional overall image of the blood tube 202. In the case where the label 203 is attached to the blood tube 202 at the side facing the camera 201 as shown in FIG. 2(A), the light irradiated from the light sources 401a, 401b scatters on the label 203 attached to the surface of the blood tube 202, and is incident on the camera 201. In the case where the image of the sample in the blood tube 202 can be picked up through the gap between the labels 203 as shown in FIG. 2(B), the light irradiated from the light sources 401a, 401b transmits through the blood tube 202, while having the wavelength partially absorbed by the serum 204 in the blood tube 202, and having the wavelength partially transmitted through the serum 204. The transmitted light further transmits through the blood tube 202, and scatters on the label 203 attached to the surface of the blood tube 202. The scattered light transmits through the blood tube 202, the serum 204, and the blood tube 202 again in this order so as to be incident on the camera 201. The image processing engine 404 is configured to execute the image processing such as the serum region extraction process from the image picked up by the camera 201 so as to identify positions and colors of the label 203 and the serum region 204. Like another example of the first embodiment, the light ray may be irradiated from the left front and right front sides of the blood tube 202.

The grip mechanism 701 grips and lifts the sample held in the blood tube holder 405, which has been transported to the sample check module. The sample is then moved by the movement mechanism 702 until it is entirely brought into the image pickup range of the camera 201. The vertical movement is controlled by the up-down control driver (up-down control) 703. As the blood tube 202 is lifted by the grip mechanism 701, the lower side of the blood tube 202 may be sufficiently illuminated. Since the blood tube holder 405 is transported on the transport line and stopped under the control of a stop mechanism and the like, the shadow of the stop mechanism and the like may give an influence on the state where the blood tube 202 is held in the blood tube holder 405. It is therefore difficult to evenly illuminate the blood tube 202. This embodiment is intended to allow the grip mechanism 701 to lift the blood tube 202 so as to be evenly illuminated.

The sample lifted by the grip mechanism 701 is rotated by the rotation mechanism 704 to change the positional relationship between the label 203 attached to the surface of the blood tube 202 and the camera 201 so as to allow the camera 201 to pick up the full circumferential image of the blood tube 202. The grip mechanism 701 and the rotation mechanism 704 constitute the rotation section. The rotating operation is controlled by the rotation control driver 705. The input/output interface 408 as the interface is used for displaying the detected index and amount of the serum, transmitting data, and inputting parameters for the serum index/amount.

Figure 8:
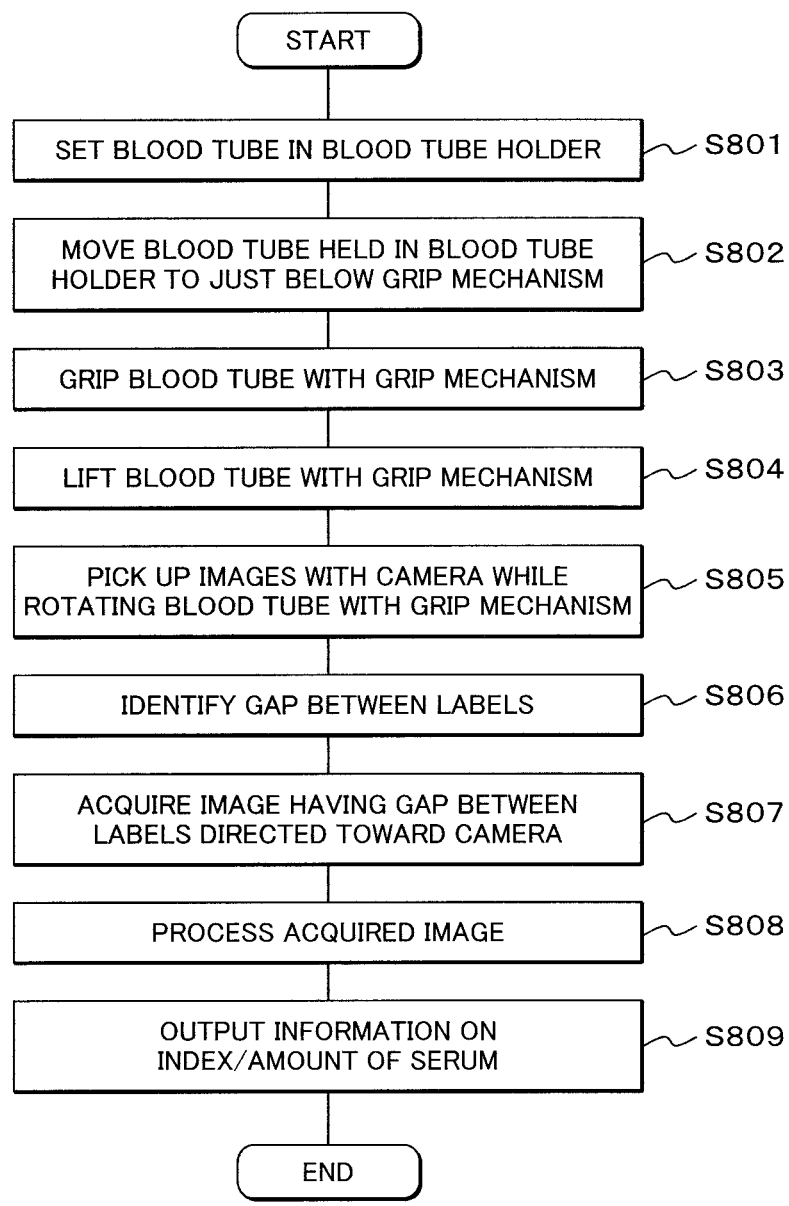
FIG. 8 is an operation flow of the sample check module according to the second embodiment.

FIG. 8 is an operation flow of the sample check module according to the second embodiment. The labeled blood tube 202 is set in the blood tube holder 405 (step S801). Then the blood tube 202 in the blood tube holder 405 is moved to just below the grip mechanism 701 (step S802). The blood tube 202 is gripped by the grip mechanism 701 (step S803), and lifted to the position which allows the camera 201 to pick up the overall image of the blood tube 202 (step S804). A plurality of images are acquired by the camera 201 while rotating the tube (step S805). The acquired images are subjected to the process executed by the image processing engine 404 for identifying the gap between the labels (step S806).

Figure 9:
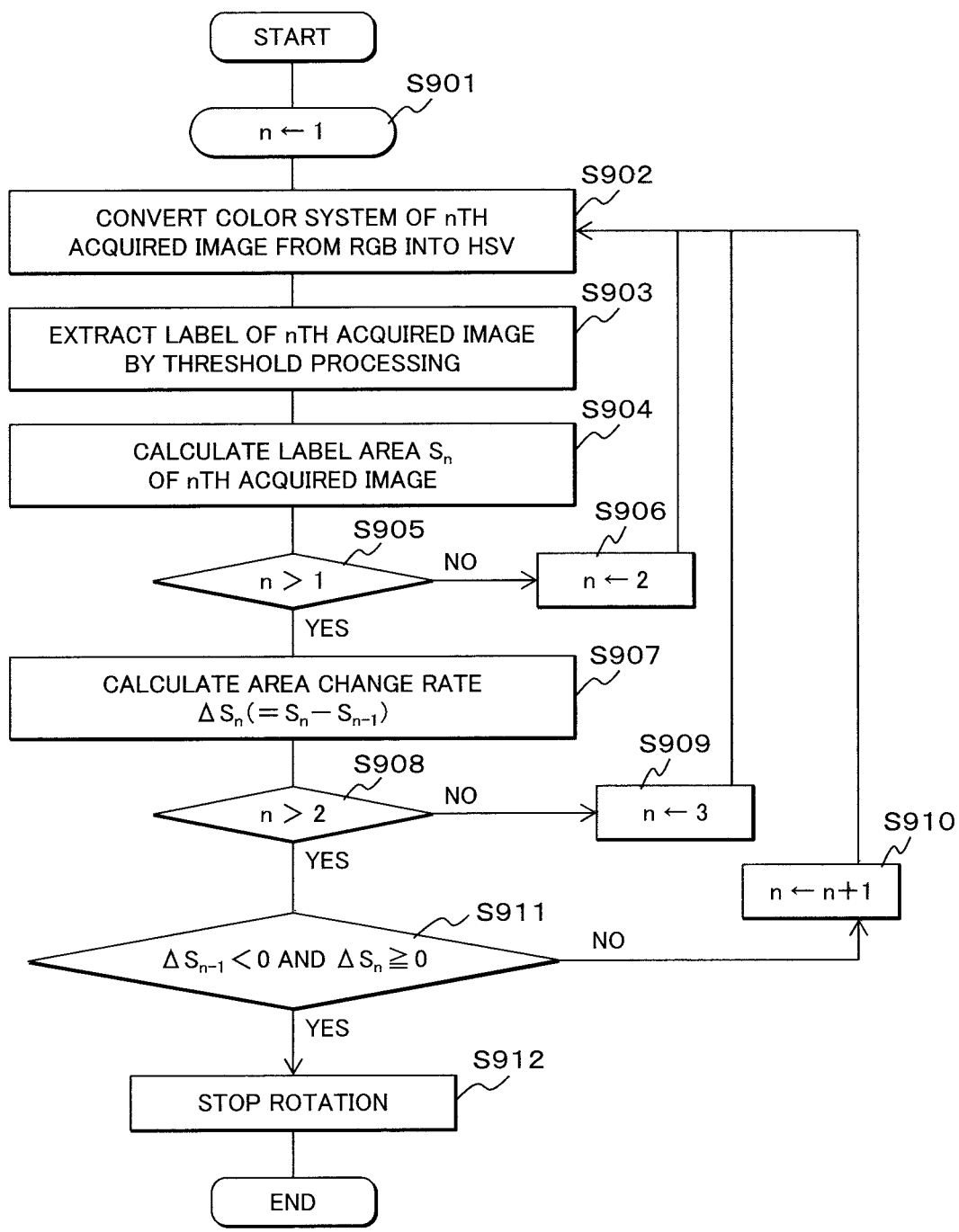
FIG. 9 is an operation flow for identifying a gap between labels according to the second embodiment.

FIG. 9 shows an example of the flow for identifying the gap between labels. FIG. 10 is an explanatory view representing change in the label area in accordance with varying direction of the blood tube according to the second embodiment. The flow is executed for each acquisition of the single image. The color system of the first acquired image is converted from RGB into HSV (step S902). The threshold process is executed to extract the label 203 as shown in FIG. 10(A) (step S903). The threshold value of the HSV color system for the label extraction is preliminarily set. A label area ($S_1$) is calculated from the extracted label region (step S904). Like the process using the first acquired image, the label area ($S_2$) is calculated from the second acquired image (step S904). Then an area change rate ($\Delta S_2$) of the label area of the second acquired image is calculated from the label area of the first acquired image (step S907). In the same way as aforementioned, each area change rate ($\Delta S_n$) of the third and subsequent acquired images will be calculated (step S907). In step S901, the value 1 is substituted for n for execution of the first acquired image. The area change rate ($\Delta S_n$) is obtained after acquisition of the second image. Therefore, the determination whether or not the image is the second and subsequent one is made in step S905. In step S906, the value 2 is substituted for n for execution of the second acquired image. In step S909, the value 3 is substituted for n for processing the third acquired image.

FIG. 10(G) shows changes in the area change rate. The x-axis represents the angle of the blood tube 202 corresponding to FIGS. 10(A) to 10(F), and the y-axis represents the label area and the label area change rate. The state indicated by FIG. 10(A) shows the largest label area, and the state indicated by FIG. 10(D) shows the smallest label area. The label area becomes smaller as the state varies from FIG. 10(A) to FIG. 10(D), and becomes larger as the state varies from FIG. 10(D) to FIG. 10(F). Upon inversion of sign of the area change rate ($\Delta S_n$) from negative to positive, it is determined that the gap between labels is directed to face the camera 201 (step S911), and rotating operation is stopped (step S912). The determination in step S911 may be made only after acquisition of the third and subsequent images. Accordingly, it is determined in step S908 whether the image is the third and subsequent one. In step S909, the value 3 is substituted for n for processing the third acquired image. In step S910, n is incremented for processing the image acquired subsequent to acquisition of the fourth and subsequent image. The threshold process is executed to extract the labeled serum region 204L having the label 203 as background, and the unlabeled serum region 204N having the background plate 406 to the rear of the blood tube 202 as background from the last acquired (step S807) image. Like the first embodiment, the determination is made with respect to the serum index, and the serum amount is calculated from the extracted labeled serum region 204L and the unlabeled serum region 204N (step S808). The results are then output (step S809).

As described in this embodiment, the image of the blood tube 202 in rotation is picked up, and the gap between the labels 203 is directed to face the camera 201. This allows acquisition of the image in the state shown in FIG. 2(B) regardless of the relationship between the camera 201 and the direction of the label 203 attached to the blood tube 202. It is therefore possible to extract the labeled serum region 204L having the label 203 as background, and the unlabeled serum region 204N having the background plate 406 to the rear of the blood tube 202 as background.

In this embodiment, the rotating operation is stopped upon determination that the gap between the labels 203 is directed to face the camera 201, which is not limited thereto. A plurality of images of the blood tube 202 in rotation at 360° are picked up, from which the picked up image directed to face the camera 201 may be selected. This embodiment is suitable for the case requiring a long time for controlling operation, as there is no need of real-time control for stopping the rotation.

The determination with respect to the gap between the labels 203 directed to face the camera 201 is made based on the label area change rate, which is not limited thereto. For example, the determination may be made that the gap between the labels 203 is directed to face the camera 201 based on the extracted image with maximum serum region area.

Third Embodiment

In the second embodiment, a plurality of images of the tube in rotation are picked up by the camera 201 so that the state shown in FIG. 2(B) is acquired. This embodiment describes the method for acquisition of the image equivalent to the one in the state shown in FIG. 2(B) from the single image using the line camera. The biological-sample analysis device according to the third embodiment is basically the same as the biological-sample analysis device 120 according to the first embodiment except the sample check module.

Figure 20:
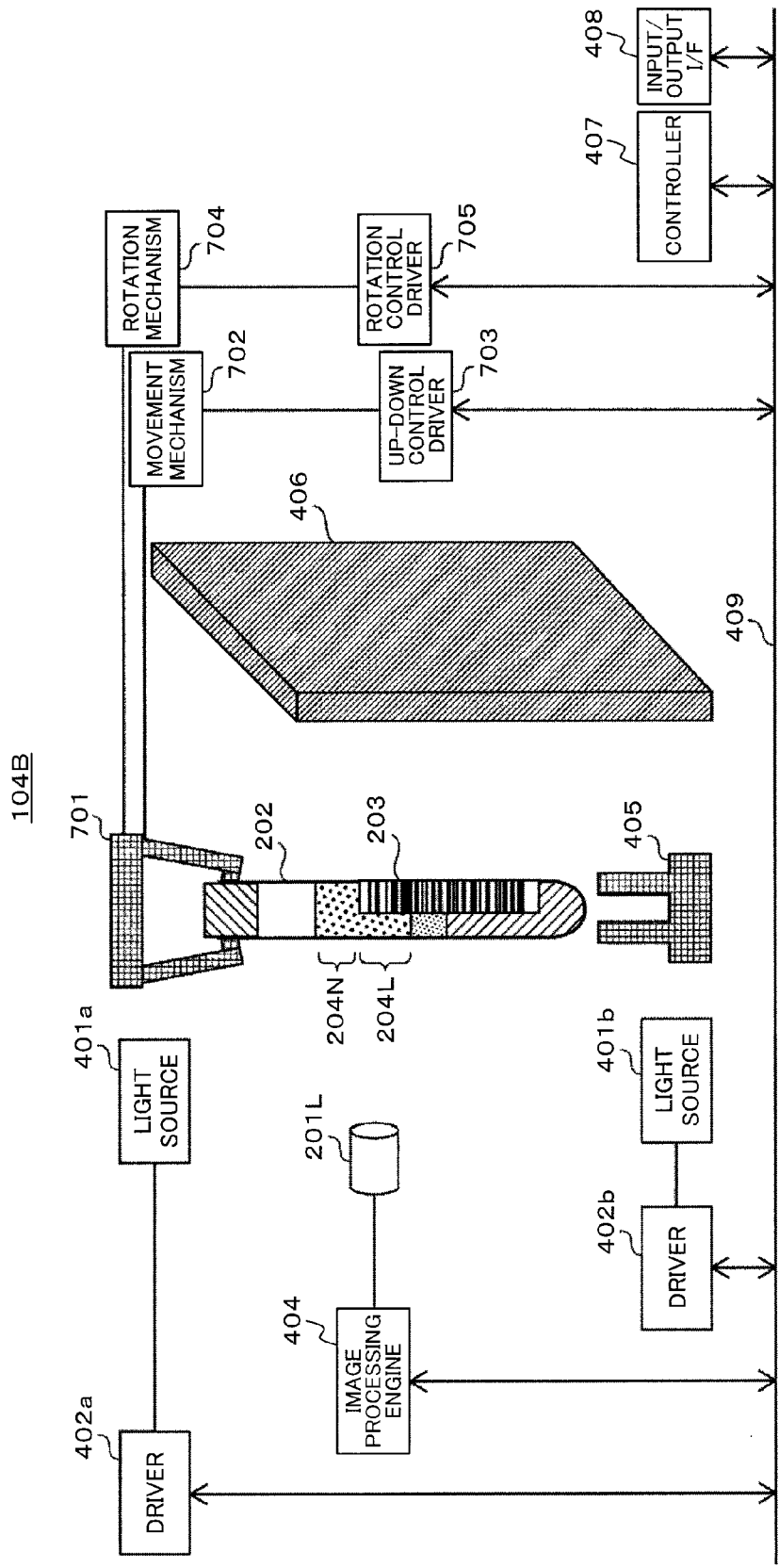
FIG. 20 is a view representing a structure of the sample check module according to the third embodiment.

FIG. 20 shows a structure of the sample check module according to the third embodiment. The sample check module 104B of the embodiment with the similar structure to that of the second embodiment uses a line camera 201L instead of the camera (area camera) 201. Like the second embodiment, it is possible to laterally irradiate the light from the left front and right front sides of the blood tube 202.

Figure 11:
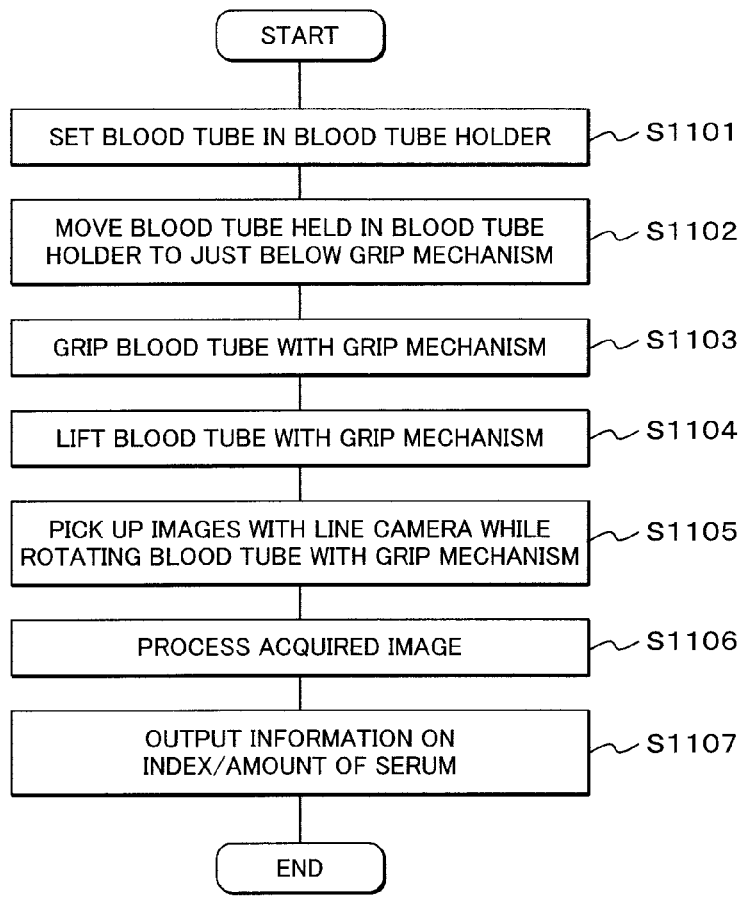
FIG. 11 is an operation flow of the sample check module according to a third embodiment.

FIG. 11 is an operation flow of the sample check module according to the third embodiment. The blood tube 202 to which the label 203 is attached is set in the blood tube holder 405 (step S1101). Then the blood tube 202 in the blood tube holder 405 is moved to just below the grip mechanism 701 (step S1102). The blood tube 202 is gripped by the grip mechanism 701 (step S1103), and is lifted to the position which allows the camera 201L to pick up an overall image of the blood tube 202 (step S1104). The single full circumferential image of the blood tube 202 in rotation is acquired by the line camera 201L (step S1105). The image processing engine 404 identifies the gap between the labels 203 from the acquired image (step S1106).

Figure 12:
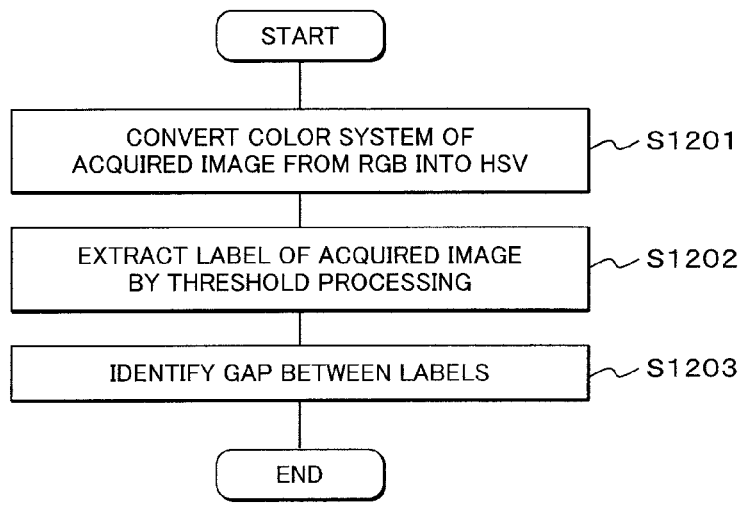
FIG. 12 is an operation flow for identifying a gap between labels according to the third embodiment.
Figure 13:
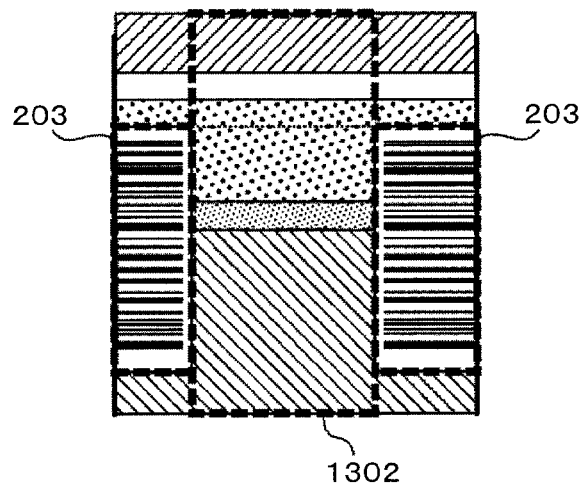
FIG. 13 is an explanatory view representing an image picked up by a line camera according to the third embodiment.

FIG. 12 shows an example of a flow for identifying the gap between labels. FIG. 13 shows an example of the image picked up by the line camera. The color system of the acquired image is converted from RGB into HSV (step S1201). The threshold value of the HSV color system for label extraction is preliminarily set. The threshold process is then executed to extract the label 203 (step S1202). A gap 1302 between the labels 203 is identified from the extraction result of the label 203 (step S1203). Thereafter, like the second embodiment, the color and amount of the serum are detected. Detection results are then output (step S1107).

As described in this embodiment, use of the line camera for picking up the full circumferential image of the sample allows execution of the process with the single image, thus eliminating the process step for calculating the label area. This makes it possible to reduce the processing time.

Fourth Embodiment

Figure 14A:
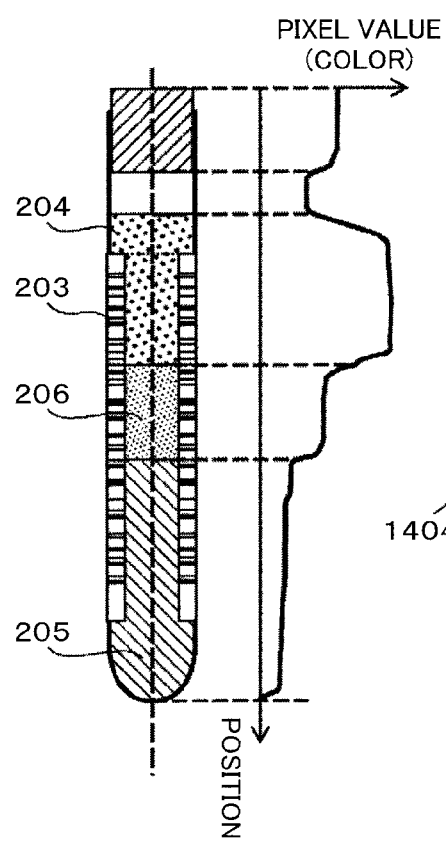
FIGS. 14A and 14B are explanatory views representing a color change rate in a blood tube axis direction according to a fourth embodiment.
Figure 14B:
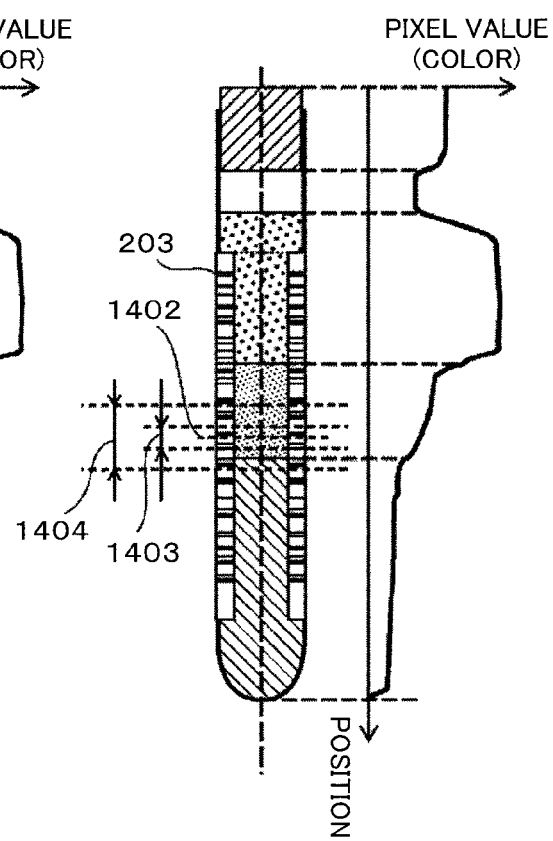

There may be the sample having the interface between serum and separating agent, and the interface between clot and separating agent inclined in the depth direction when seen from the camera. FIG. 14 shows an example of the color change rate in the blood tube axis direction. If the interface is not inclined, the color change rate in the blood tube axis direction is brought into the state as shown in FIG. 14(A). Meanwhile, if the interface is inclined in the depth direction when seen from the camera, the color change rate in the blood tube axis direction becomes smaller than that of the interface with no inclination as shown in FIG. 14(B). This may cause misidentification of the position of the interface between clot and separating agent. The phenomenon which will be observed in the case of the interface between serum and separating agent is similar to the one observed in the interface between clot and separating agent as shown in FIGS. 14(A) and 14(B). In this embodiment, if the color change rate around the interface is lowered below the specific threshold value, it is determined that the interface is inclined in the depth direction when seen from the camera. Therefore, the position at which the color change rate exceeds another threshold value is determined as the interface. This embodiment will be described based on the sample check module of the biological-sample analysis device according to the second embodiment.

Figure 15:
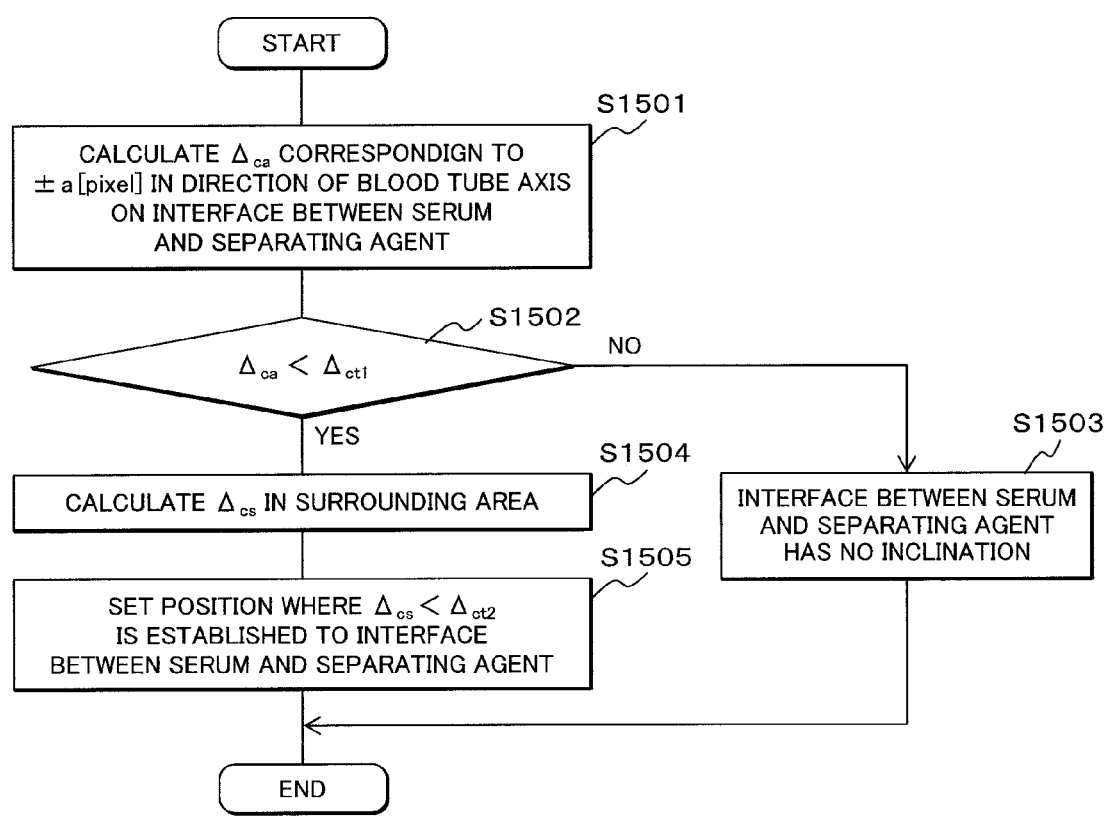
FIG. 15 is an operation flow for detecting an interface between serum and separating agent using the color change rate according to the fourth embodiment.

FIG. 15 is a flow for detecting the interface between serum and separating agent using the color change rate. The blood tube 202 is rotated by the grip mechanism 701, having its image picked up by the camera 201. The gap between the labels 203 is identified by the image processing engine 404 so as to extract the labeled serum region 204L having the label as background, and the unlabeled serum region 204N having the background plate 406 to the rear of the blood tube 202 as background, respectively. Thereafter, the serum liquid surface and the interface between serum and separating agent are detected from the color information with respect to the labeled serum region 204L and the unlabeled serum region 204N. The color change rate ($\Delta$ca) in the blood tube axis direction corresponding to ±a pixels is calculated from the axis of the interface between serum and separating agent like calculation of the color change rate ($\Delta$ca) in the blood tube axis direction corresponding to ±a pixels 1403 from the axis 1402 of the interface between clot and separating agent as shown in FIG. 14(B) (step S1501). The color change rate ($\Delta$ca) is compared with the threshold value ($\Delta$ct1) (step S1502). If the color change rate ($\Delta$ca) is larger than the threshold value ($\Delta$ct1), it is determined that the interface between serum and separating agent is not inclined (step S1503). If the color change rate ($\Delta$ca) is smaller than the threshold value ($\Delta$ct1), the color change rate (Acs) in the surrounding area corresponding to ±a pixels is calculated from the axis of the interface between serum and separating agent like the calculation of the color change rate (Acs) in the surrounding area 1404 as shown in FIG. 14(B) (step S1504). The position at which the color change rate (Acs) becomes smaller than the threshold value ($\Delta$ct2) is determined as the interface between serum and separating agent (step S1505).

Even if the interface between serum and separating agent is inclined in the depth direction when seen from the camera, the embodiment allows identification of the interface position by using the color change rate in the blood tube axis direction. This embodiment is applicable to the sample check module in the biological-sample analysis device according to the third embodiment.

Fifth Embodiment

In the case where the image of the blood tube is picked up either by the area camera or the line camera, the width of the gap between labels varies with the relationship between the label size and the blood tube diameter. The width of the label attached to the tube at the camera side will vary with the gap width. In accordance with the width of the label attached to the tube at the camera side, the light from the light source transmitting through the blood tube and the serum, and scattering on the label may vary the luminous energy of the light which retransmits through the serum and the blood tube, and the shadow area of the label formed in the serum region. The resultant images picked up by the camera have different colors in spite of the same serum index. This embodiment will describe the method for determining the serum region color using the width of the gap between labels as the parameter. The embodiment will be described based on the sample check module of the biological-sample analysis device according to the second and the third embodiments.

Figure 16:
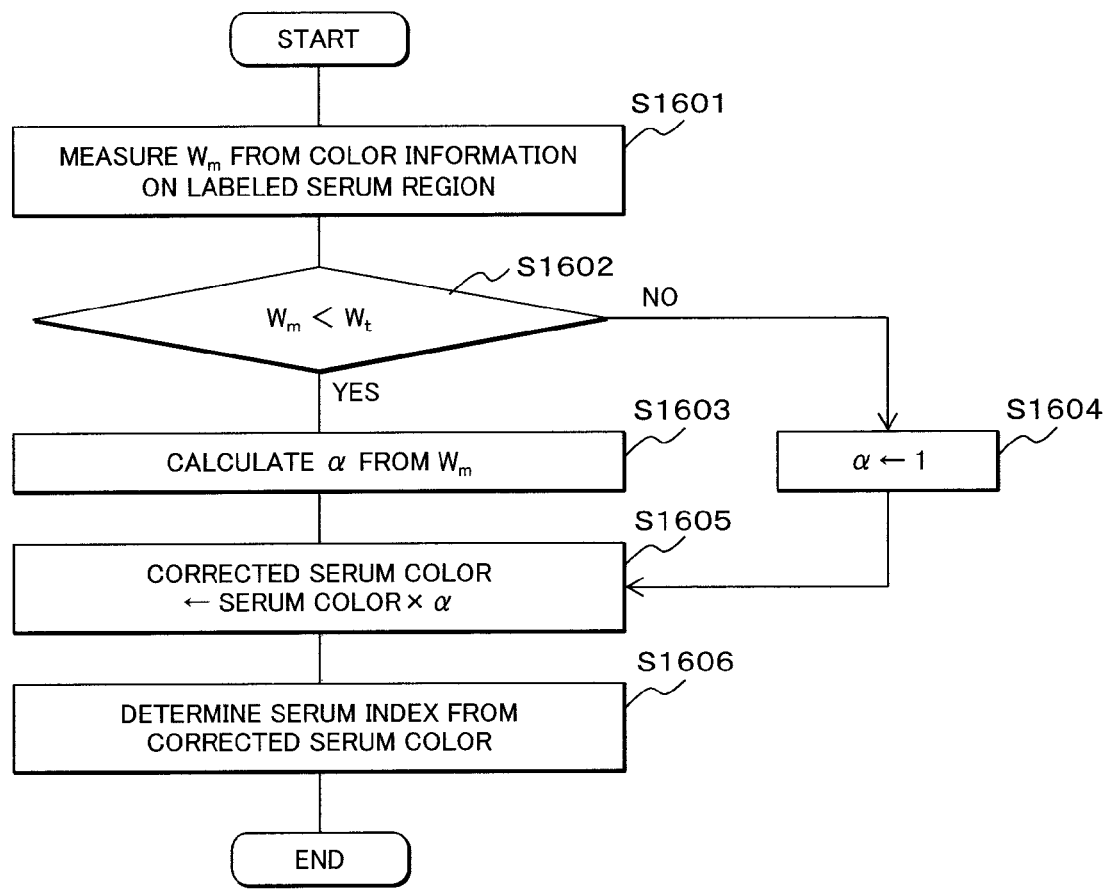
FIG. 16 is a flow for color determination with respect to a serum region using width of the gap between labels as a parameter according to a fifth embodiment.
Figures 17A, 17B:
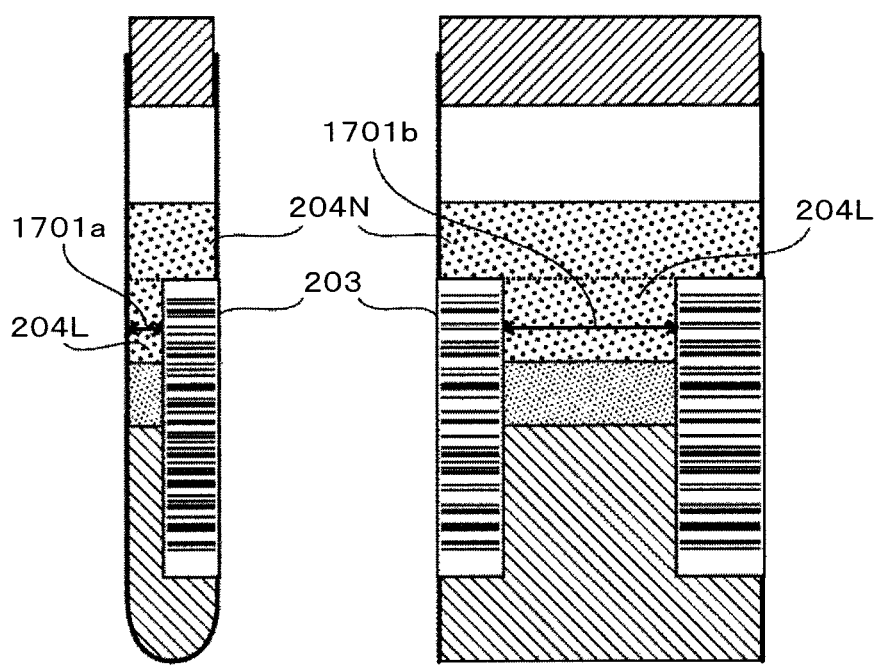
FIGS. 17A and 17B are explanatory views representing the width of the gap between labels according to the fifth embodiment.

FIG. 16 is a flow for determining the serum region color using width of the gap between labels as the parameter, and FIG. 17 is an explanatory view of the color determination process. FIG. 17(A) shows an image picked up by the area camera, and FIG. 17(B) shows an image picked up by the line camera. The blood tube 202 is rotated by the grip mechanism 701, and has its image picked up by the cameras 201 and 201L. The image processing engine 404 identifies the gap between the labels 203 so as to extract the labeled serum region 204L having the label 203 as background, and the unlabeled serum region 204N having the background plate 406 to the rear of the blood tube 202 as background, respectively. Then each width (Wm) 1701a, 1701b of the gap between the labels 203 is measured from the color information with respect to the labeled serum region 204L as shown in FIGS. 17(A) and 17(B) (step S1601). The respective gap width values (Wm) 1701a and 1701b are compared with a threshold value (Wt) (step S1602). If each gap width (Wm) 1701a, 1701b is smaller than the threshold value (Wt), a correction coefficient (a) by which the serum color is multiplied is calculated from the gap width (Wm) 1701a, 1701b (step S1603). If each gap width (Wm) 1701a, 1701b is larger than the threshold value (Wt), the correction coefficient (a) by which the serum color is multiplied is set to 1 (step S1604). The serum color is multiplied by the correction coefficient (a) to calculate the corrected serum color (step S1605) so that the serum index is determined from the corrected serum color (step S1606). The calculation formula for correction, which has been described in this embodiment, is one of examples. It is possible to carry out the correction using any other calculation formula.

The embodiment allows determination of the serum index regardless of the width of the gap between labels. In this embodiment, the gap width between labels has been described with respect to the radial direction of the blood tube. However, the serum index in the blood tube axis direction may also be determined based on the similar concept as described above.

Sixth Embodiment

In the case where the blood tube is rotated, having a plurality of images picked up by the area camera, the width of the label attached to the blood tube at the camera side largely varies with direction of the blood tube. In accordance with the width of the label attached to the tube at the camera side, the light from the light source transmitting through the blood tube and the serum, and scattering on the label may vary the luminous energy of the light which retransmits through the serum and the blood tube, and the shadow area of the label formed in the serum region. The resultant images picked up by the camera have different colors in spite of the same serum index. This embodiment will describe the method for determining the serum region color using the blood tube direction as the parameter. In this embodiment, the explanation will be made based on the sample check module in the biological-sample analysis device according to the second embodiment.

Figure 18:
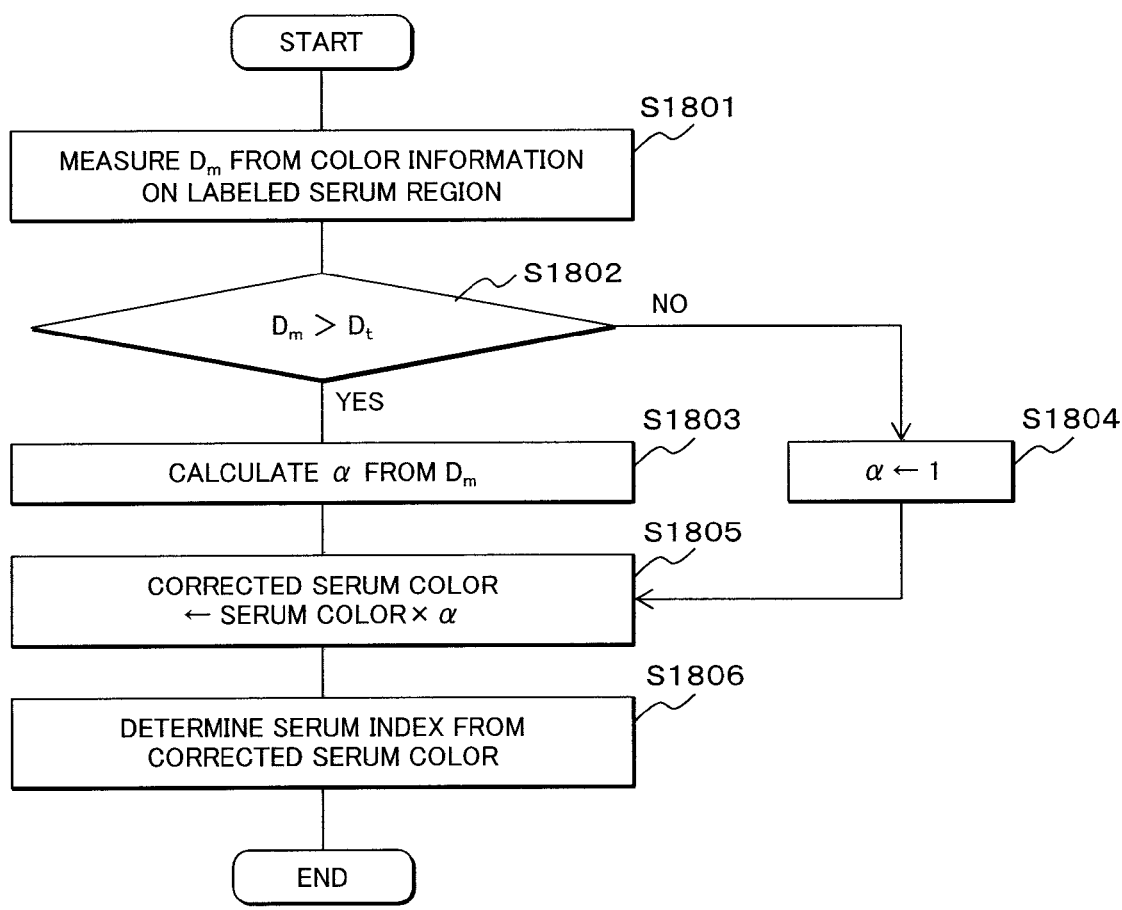
FIG. 18 is a flow for color determination with respect to the serum region using direction of the blood tube as a parameter according to a sixth embodiment.
Figure 19:
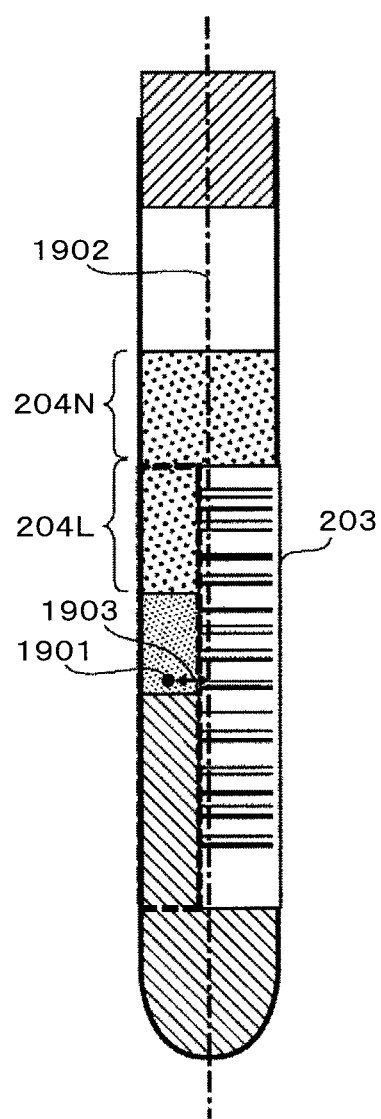
FIG. 19 is an explanatory view representing a distance of center of gravity of the gap between labels from the blood tube axis.

FIG. 18 is a flow for determining the serum region color using the blood tube direction as the parameter, and FIG. 19 is an explanatory view of the color determination process. The blood tube 202 is rotated by the grip mechanism 701, having its image picked up by the camera 201. The image processing engine 404 identifies the gap between the labels 203 to extract the labeled serum region 204L having the label 203 as background, and the unlabeled serum region 204N having the background plate 406 to the rear of the blood tube 202 as background, respectively. Then, a distance (Dm) 1903 between a center of gravity 1901 of the gap between the labels 203, and a blood tube axis 1902 is measured from the color information with respect to the labeled serum region 204L as shown in FIG. 19 (step S1801). The distance (Dm) 1903 is compared with a threshold value (Dt) (step S1802). If the distance (Dm) 1903 is larger than the threshold value (Dt), the correction coefficient (a) by which the serum color is multiplied is calculated from the distance (Dm) 1903 (step S1803). If the distance (Dm) 1903 is smaller than the threshold value (Dt), the correction coefficient (a) is set to 1 (step S1804). The serum color is multiplied by the correction coefficient (a) to calculate the corrected serum color (step S1805). The determination is made with respect to the serum index from the corrected serum color (step S1806). The calculation formula for correction as described above is one of examples, and correction may be executed in accordance with any other calculation formula.

Seventh Embodiment

Selection of black as color of the background plate for preventing reflection of the illumination light, for example, may provide the effect for suppressing formation of shadow of the cap and the label of the blood tube in the serum region. However, upon image pickup of the sample with low brightness such as jaundice (dark yellow), a sufficient color difference between the unlabeled serum region and the background plate cannot be obtained, which may cause extraction error of the serum region. This embodiment will describe the method which can be applied to the process for picking up the image of the sample with low brightness by using the background plate in the color with high brightness, for example, white.

The white background plate exhibits high reflectance, thus requiring the process for reducing the specular reflection on the background plate. For example, there has been proposed the method of attaching the material formed by painting the polycarbonate white. It is also effective to execute the matting process, or treating the surface of the background plate so as to prevent the specular reflection.

The embodiment provides the image which allows detection of the index and the liquid amount of the serum by reducing the specular reflection light in spite of the white background plate in use.

This embodiment explains use of the white background plate. However, such color does not have to be set to white strictly. Any color may be selected so long as it exhibits the brightness which gives a clear difference from the sample with low brightness up to a certain level. This embodiment may be applied to the sample check module in the biological-sample analysis device according to the first to the third embodiments as well as the fourth to the sixth embodiments.

The present invention made by the inventors has been specifically described based on embodiments as described above. However, it is to be understood that the present invention is not limited to those described above, but may be modified in various forms without departing from the scope of the invention.

LIST OF REFERENCE SIGNS

100 pre analytical system
101 transport line
102 load module
103 centrifugal separation module
104, 104A, 104B sample check module
105 unplug module
106 labeler
107 aliquoter module
108 plug module
109 classification module
110 storage module
111 control PC
112 automatic analyzer
120 biological-sample analysis device
201 camera (area camera)
201L line camera
202 blood tube
203, 203a, 203b, 203c label
204 serum (serum region, first component)
204L serum region having label as background
204N serum region having background plate as background
205 clot (clot region, second component)
206 separating agent
207 cap
401a, 401b light source
402 light source driver
404 image processing engine
405 blood tube holder
406 background plate
407 controller
408 input/output interface
409 data bus
701 grip mechanism
702 movement mechanism
703 up-down control driver
704 rotation mechanism
705 rotation control driver
1302 gap between labels
1402 axis of interface between serum and separating agent
1403 corresponding to ±a pixels from axis of interface between serum and separating agent
1404 surrounding area corresponding to ±a pixels from axis of interface between serum and separating agent
1701a, 1701b width of gap between labels
1901 center of gravity of gap region between labels
1902 blood tube axis
1903 distance between center of gravity region between labels and blood tube axis

The invention claimed is:

1. A detection device configured to execute a detection process with respect to a sample stored in a labeled container and comprising a first component and a second component which have been centrifugally separated, the detection device comprising:
   a rotation section for rotating the container,
   an image pickup section for picking up an image of the container in rotation;
   a background section serving as a background of the image pickup section; and
   a detection section for detecting color of the sample, and
   wherein the container is disposed between the image pickup section and the background section;
   the detection section identifies a first region of the sample having the label as background, and a second region of the sample having the background section as background and the detection section detects a gap region, which is not covered with the label, and calculates a center of gravity of the gap region; and
   color information of the first region of the sample having the label as background is corrected based on a distance between the center of gravity of the gap region and a center axis of the container.

2. The detection device according to claim 1, wherein a reflectance in a visible light region on the background section is 10% or lower.

3. The detection device according to claim 2, wherein the background section is colored black.

4. The detection device according to claim 1, wherein
the detection section is configured to detect the first region, and a position of an interface of the first component based on the second region information.

5. The detection device according to claim 4, wherein an amount of the first component is calculated from the position of the interface of the first component.

6. The detection device according to claim 4, wherein the detection section detects a serum as the first component.

7. A biological-sample analysis device comprising the detection device according to claim 6, wherein the serum is subjected to an aliquot process using the interface position information for analyzing the serum.

8. The detection device according to claim 4, wherein the detection section is configured to calculate a color change rate in a surrounding area of an interface between the first and the second components of the sample in an axial direction of the container so that each amount of the first and the second components of the sample is corrected based on the color change rate information.

9. The detection device according to claim 1, comprising an irradiation section for irradiating the container with a light ray,
wherein the irradiation section includes two irradiation elements; and
the two irradiation elements are used to irradiate light rays from an upper and lower position at the same side of the container.

10. The detection device according to claim 1,
wherein the image pickup device is formed by a line camera for picking up a one-dimensional image; and
the rotation section rotates the container while allowing the line camera to pick up a full circumferential image of the container.

11. The detection device according to claim 1,
wherein the detection section calculates a width of the gap which is not covered with the label.

* * * * *